United States Patent [19]

Turner

[11] 4,170,609

[45] Oct. 9, 1979

[54] ALDOL CONDENSATION PROCESS

[76] Inventor: William F. Turner, 5234 Heathercrest, Houston, Tex. 77045

[21] Appl. No.: 805,772

[22] Filed: Jun. 13, 1977

Related U.S. Application Data

[63] Continuation-in-part of Ser. No. 691,760, Jun. 1, 1976, abandoned, which is a continuation-in-part of Ser. No. 389,907, Aug. 20, 1973, abandoned.

[51] Int. Cl.$^2$ ............................................. C07C 45/00
[52] U.S. Cl. ........................... 260/586 C; 260/590 E; 260/593 R; 260/601 R; 260/592
[58] Field of Search ........... 260/593 R, 586 R, 590 E, 260/590 G, 601 R

[56] References Cited

U.S. PATENT DOCUMENTS 2,829,168  4/1958  Lowes ............................... 260/593 R

OTHER PUBLICATIONS

Seebald et al., Archio der Pharmazie, vol. 305, pp. 406–417, (1972).
Kozima et al., Nippon Kogaku Kaishi, 1974, (7), pp. 1353–1355, (1974).

*Primary Examiner*—James H. Reamer
*Attorney, Agent, or Firm*—Michael P. Breston

[57] ABSTRACT

In a process for the aldol condensation and dehydration of carbonyl compounds, and for the substitution of carbonyl compounds onto the alpha carbon of alpha-beta unsaturated carbonyl compounds, carbonates of aluminum are used. The aluminum oxycarbonate catalyst may be either in a fixed or fluid bed.

14 Claims, No Drawings

ALDOL CONDENSATION PROCESS

This application is a continuation-in-part of my co-pending application Ser. No. 691,760 filed on June 1, 1976 and now abandoned, which is a continuation-in-part of application Ser. No. 389,907 filed on Aug. 20, 1973 and now abandoned.

BACKGROUND OF THE INVENTION

1. Field of the Invention

The present invention is directed to a process for the aldol condensation of carbonyl compounds, and for the substitution of a different carbonyl compound into the aldol condensation products.

2. Prior Art

The aldol condensation process is a well known commercial process for increasing the molecular weight of carbonyl compounds. It is used for the condensation of the same compounds or for the condensation of a mixture of compounds. The catalyst commonly used for aldol condensation is sodium hydroxide or other caustic material. Aldol condensations generally yield hydroxy carbonyl compounds. These compounds are usually dehydrated to the unsaturated carbonyl compound using an acid catalyst, e.g., acetone is condensed with a base to yield diacetone alcohol which is treated with an acid and dehydrated to mesityl oxide. The salt thereby produced is then filtered and then disposed. No catalyst suitable for commercial scale condensation of higher ketones (e.g. methyl isobutyl ketone) is known.

Schonberg and Jugens, Berichte 95, 2137–40 (1962); Tanaube et al., Chemical and Pharmaceutical Bulletin, II pp. 536; and Miller's U.S. Pat. No. 2,800,510 may have suggested preparing hydroxy carbonyl compounds without subsequent dehydration using an aluminum oxide catalyst. Prior art has also suggested reasonably efficient methods of condensing higher aldehydes with ketones (U.S. Pat. No. 2,000,017 and British Pat. No. 440,539).

Palmer and Cowan (British Pat. No. 921,510) suggest using an alkali-treated, activated-alumina catalyst (which could also be calcium chloride treated) to convert acetone to a mixture of mesityl oxide and diacetone alcohol. The catalytic effect in this case was due to the alkali, as zero conversion to mesityl oxide was reported when alkali treatment was omitted. Kojima (Nippon Kogake Koushi, 1974(7) Pgs. 1353-1355 suggests use of aluminum oxide treated with hydrochloric acid to obtain low yields of aldol condensation products.

Other patents of interest are:

| U.S. Pat. No. | | | British |
|---|---|---|---|
| 1,437,139 | 2,442,280 | 3,155,730 | 783,458 |
| 1,151,113 | 2,468,710 | 3,361,828 | 922,826 |
| 1,885,221 | 2,684,385 | 3,422,072 | |
| 2,130,592 | 2,719,863 | 3,432,557 | |
| 2,275,586 | 2,829,168 | 3,542,878 | |
| 2,376,070 | 3,002,999 | 3,544,635 | |
| | 3,077,500 | | |

As will be apparent from the above cited art, benefits of aldol preparation by carbon dioxide addition to aluminum compounds have not been previously recognized.

SUMMARY OF THE INVENTION

The present invention is directed to a process for condensing carbonyl compounds using aluminum oxycarbonate as the catalyst. Aluminum oxycarbonate is a solid material with catalytic activity over a substantial period of time. The invention herein described combines the aldol condensation and dehydration into one step using a fixed or fluid bed reactor. Degradation of the catalyst is avoided when the reaction is stopped by application of $CO_2$ to displace carbonyl liquid and vapors during shutdown.

The aluminum oxycarbonate catalyst in either a fixed or fluid bed is used to substitute carbonyl groups onto the alpha carbon of alpha-beta unsaturated carbonyl compounds which may have been prepared as aldol condensation products.

DESCRIPTION OF THE PREFERRED EMBODIMENTS

As used herein, "aldol condensation" refers to the condensation of aldehydes, ketones and mixtures of aldehydes and ketones with the simultaneous dehydration of the condensation product.

As used herein, "fixed bed" means a stationary catalyst bed through which vapors and liquids move in the practice of the invention, and "fluid bed" means a suspension of catalyst particles maintained by movement of the reactants.

The process of the present invention may be used to condense a wide variety of aldehydes and ketones. Carbonyl compounds containing from two to twenty carbon atoms are particularly desirable for condensation, however, even higher molecular weight carbonyl compounds may be used. Although it is generally desired to condense one molecular species, for instance an aldehyde, it is also possible to condense different molecular species, that is, an aldehyde with a different aldehyde, an aldehyde with a ketone, or a ketone with a different ketone. When more than one molecular species of reactant is used, a mixture of products is usually produced. The proportion of each species of reactant used and their relative activities for the condensation reaction control the product distribution.

With the aluminum oxycarbonate catalyst of the present invention, the differences in reactivity between lower and higher molecular weight carbonyl compounds do not appear as distinct as when catalysts of the prior art are used. Therefore, the carbonyl compounds for carrying out the aldol condensation process according to the present invention are those having the following general formula when one molecular species is used:

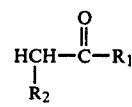

$R_1$, and $R_2$ can be the same or different and are selected from the group consisting of hydrogen, alkyl, alkylene, cycloalkyl, aryl, alkaryl, and aralkyl groups.

If two or more different aldehydes and/or ketones are used, at least one of them must have the structure prescribed by the above formula.

According to the present invention, the catalyst used is aluminum oxycarbonate. The aluminum oxycarbonate may be prepared from aluminum hydroxide which is dehydrated and calcined at about 900° C. in a carbon dioxide atmosphere which tends to coat the individual aluminum oxide ($Al_2O_3$) particles with a thin layer of aluminum oxycarbonate approximating the formula $[Al_2(OH)_5]_2 CO_3.H_2O$. Calcining $Al_2O_3$ in a $CO_2$ atmosphere also gives a suitable catalyst.

Many other processes would yield a suitable catalyst, including treating aluminum oxide or hydroxide with $CO_2$ at ambient or elevated temperatures. The $CO_2$ treatment may be at atmospheric or elevated pressure. The aluminum compound may be treated dry or wetted with water or with a carbonyl compound. Catalytic activity of the aluminum oxide improves rapidly with the initial addition of $CO_2$ but soon reaches a very efficient state that improves little thereafter. The ratio of $Al/CO_2/O$ can vary widely. Some $CO_2$ treatment is essential. Commercial activated alumina may contain enough carbonate but oftentimes needs treatment with $CO_2$ to improve its catalytic activity.

The aluminum oxycarbonate catalyst may be employed in such suitable forms as, for example, granules, pellets, powders, etc., of any workable size. In using the aluminum oxycarbonate catalyst in the process of the present invention, the catalytic material in the desired size of particles or granules is preferably packed into a suitable reaction tube or chamber. The catalytic material thus acts as a fixed bed over which both the vapor or liquid carbonyl compounds may be passed in carrying out the condensation reaction. However, the catalytic material may also be used as a fluid bed type catalyst. Suitable heating means may be used to maintain the desired operating temperature in the zone where the catalytic material is present; however, the temperatures for the condensation reaction may also be obtained from the heating of the carbonyl compounds external to the reaction zone.

The temperature at which the condensation reaction is conducted generally falls within the broad range of about 0° to about 200° C. or more with a preferred temperature range from about 80° C. to about 150° C. At the lower temperature the reaction speed is slow, but too high a temperature is avoided to prevent side reactions. The reaction, furthermore, is conducted at a temperature at which the reactant and product are stable. For example, aldehyde begins to decompose at about 250° C. The pressure used in the condensation reaction may vary from sub-atmospheric to about 50 atmospheres. The preferred pressure range is from 1 to about 20 atmospheres. As is apparent from the temperature and pressure ranges and the class of carbonyl compounds suitable as feeds, the carbonyl compound may exist either in the gas or the liquid phase during the reaction. Preferred conditions include gas and liquid passing countercurrent thru the catalyst bed.

The preferred conditions are such that the water of reaction, as well as any previously adsorbed water, is azeotropically removed from the catalyst. Removal of water in contact with the catalyst is essential to maintain the high reactivity of the catalyst. For carbonyl compounds that azeotrope with and are insoluble or have limited solubility in water, it is convenient to operate at atmospheric pressure and at a temperature at or near the normal boiling point of the carbonyl compound. With compounds such as acetone which do not azeotrope well with water at these pressures and temperatures, the pressure may be raised so that the water will azeotrope and a solvent may be added to aid in azeotroping and separating the water. The addition of such solvents is a well known practice to those familiar with the art, and no further description thereof is required. Under these conditions, the hot vapors coming up through the bed furnish sufficient energy to carry over the water of reaction, with water separating from the condensate, while the refluxing liquid removes the product from the bed.

In the fixed bed reaction, it is also desirable to remove the product from the proximity of the catalyst to avoid further polymerization of the product. The concentration of the product may be up to 75% or more based on the total amount of product plus raw materials. Fluid must continue to flow across the bed to remove the product. If the catalyst bed is maintained above the boiling points of water and the raw materials while hot vapors flow through the bed, dark polymers or tars are formed.

In general, pressures of 1 to 10 atmospheres will establish the boiling points of the carbonyl compounds in the desired 80° to 150° C. operating range. For high boiling carbonyl compounds, sub-atmospheric pressures may be used or a fluid bed of the aluminum oxycarbonate catalyst may be employed. In fluid bed reactors it is preferred to remove the reactant solution at product concentrations of 75% or below to limit the formation of higher molecular weight products.

The aluminum oxycarbonate catalyst under the above described conditions acts efficiently to substitute one carbonyl compound onto he alpha carbon of alpha-beta unsaturated carbonyl compounds, which may be previously prepared aldol condensation products. Any undesired byproducts may thus be recycled through the process and recovered.

Carbonyl compounds that are expensive or inconvenient to use in the process for any reason may be substituted into a condensation product under the described conditions or even milder conditions, for example by simply contacting the reactants with the catalyst.

The present invention will be further illustrated by the following specific examples which are given by way of illustration and not as limitations on the scope of the invention.

EXAMPLE 1

The following equipment was used to form an aldol condensation pilot unit: a two feet high pot having a feed inlet at the top and a product outlet at the bottom had a steam coil within the pot to control the temperature. Extending upwardly out of the pot were a series of pipes. The first section "A" was a six inch pipe of about 18"; section "B" was 24" of six inch pipe; section "C" was 60" of four inch pipe and a water cooled condenser was fitted to the top of the sections of pipe. The condenser had a return to a receiver for separation of the water and a recycle connected to an inlet at the top of section "C".

Section "A" was packed with one-half inch porcelain saddles. Section "B" was packed nine and one-half inches deep (eight and one-half pounds) with five to ten millimeter aluminum oxycarbonate. Section "C" was packed with one-half inch porcelain saddles.

Charged into the pot was 121 LB of methyl isobutyl ketone (MIBK). The reflux was maintained at approximately 1.5 LB/min. After running three hours, about 50 LB MIBK was in the receiver and water was beginning to separate. Water separation continued for an additional eight hours at approximately 70 ml/hr. The total run time was 11 hours. The pot temperature at the end of the run was 259° F. indicating approximately 20 LB of 2, 6, 8-trimethyl-5-nonen-4-one (TMNO) in the pot. The rate of TMNO production was approximately 9 LB/ft$^2$/hr.

EXAMPLE 2

Using the same equipment as in Example 1, section "B" was packed with 22" of fresh ¼" by ½" aluminum oxycarbonate. The top 10" of Section "A" was emptied of saddles and packed with aluminum oxycarbonate. The total catalyst charge was 27-1/2LB.

Charged to the apparatus as described was 121 LB of MIBK. The pot was maintained at 300° F. by continuous feed and product removal. A total run time of 260 hours resulted in a total product removal of 3,280 LB consisting of 1,093 LB MIBK, 2,153 LB TMNO and 44 LB of higher boiling material. The condensation of the MIBK was at a 98% yield with an average rate of 40 LB/ft$^2$/hr.

EXAMPLE 3

The equipment was the same as in Example 2 but with section "C" changed from a four inch to a six inch pipe. The section "C" was packed with 49" of aluminum oxycarbonate. The unit thus had the catalyst in each of the sections or beds. The total amount of the catalyst was 72 LB (81 inches of ¼" by ½") aluminum oxycarbonate.

The pot was maintained at 300° F. by continuous addition of MIBK and product removal. The condensation reaction was carried out for a total of eighty and one-half hours. The total product obtained was 1,808 LB consisting of 586 LB MIBK, 1,180 LB TMNO and 42 LB of higher boiling material. This resulted in a condensation yield of 96.6% with a rate of approximately 73 LB/ft$^2$/hr.

From the foregoing examples, it is seen that the reaction rate may be controlled by the catalyst depth. Further, the by-product concentration may be limited by limiting the conversion per pass or concentration of product in contact with the catalyst. This concentration is easily determined by the increase in the boiling point which occurs with increased product concentration.

EXAMPLES 4–9

The following equipment was used to form an aldol condensation pilot unit:

A pot approximately 40" tall had extending therefrom a 24" first section of six inch pipe, a 56" second section, and a 12" third section which was a neck down section from the six inch to four inch pipe. Above the sections of pipe was a water-cooled condenser. The bottom 24" of the unit was packed with INTALOX saddles. The catalyst bed was 56" of ¼" by ½" aluminum oxycarbonate.

To the pot was charged 40 LB of normal pentane and 160 LB of acetone. The reflux conditions were set so as to obtain a reflux rate of approximately 1.6 LB/min. The pressure was varied on the reactor resulting in varied reflux temperatures. As the pressure was increased, the conversion rates increased as set forth in Table 1.

TABLE I

| Example | Pressure, psig | Approx. Conversion Rate, LB/ft$^2$/hr. |
|---------|----------------|----------------------------------------|
| 4 | 30 | 7.5–11 |

TABLE I-continued

| Example | Pressure, psig | Approx. Conversion Rate, LB/ft$^2$/hr. |
|---------|----------------|----------------------------------------|
| 5 | 40 | 9.0–15 |
| 6 | 50 | 15.0 |
| 7 | 60 | 16.0–19 |
| 8 | 70 | 22.5 |
| 9 | 80 | 30.0–33 |

EXAMPLE 10

The following equipment was used to form an aldol condensation pilot unit:

A 40" pot had extending thereform sections os six inch pipe, a 40" section, a 120" section, and a 56" section, respectively. Above the sections of pipe was a water cooled condenser. INTALOX saddles were changed into the bottom 40" section and the top 56" section. A fixed bed of aluminum oxycarbonate was charged to the 120" section.

The unit was run charging acetone to produce mesityl oxide, using pentane or petroleum ether to aid in the azeotropic removal of the water of reaction. Extended runs at 100 psig pressure averaged 100 lb. mesityl oxide/hr./ft$^2$ with no diacetone alcohol. Utilizing the unit after the acetone condensation runs and without changing the catalyst, MIBK was continuously fed to the pot and product removed at such a rate as to keep the pot refluxing at 300° F. at atmospheric pressure for 23 hours. The reaction produced TMNO at a reaction rate of 94 LB/ft$^2$/hr. This example illustrates the long activity of the catalyst even when used at varying conditions. $CO_2$ was added to the unit each time it was shut down.

EXAMPLE 11

Utilizing the same equipment as in Example 10, reflux was carried out for two and one-half hours followed by a purge with carbon dioxide at 40 psig $CO_2$ pressure overnight. MIBK was then continuously fed and product taken off resulting in a conversion rate of more than 100 LB/ft$^2$/hr.

This example illustrates that the reactivity of the catalyst may be enhanced by a simple $CO_2$ purge to reactivate the catalyst as shown by the increased conversion rate.

EXAMPLE 12

A three liter flask equipped with stirrer was utilized to produce a fluid bed. Charged to the flask was 1 kg. of MIBK and 100 g. of aluminum oxycarbonate (fine powder). The flask was heated to an initial boiling point of 115° C. wherein the MIBK and water began to azeotrope with the removal of 67 ml. of MIBK saturated with water. Thereafter MIBK was continually refluxed to the flask. Over a ten hour period the pot temperature increased from 115° C. to about 145° C. From the reaction pot, 760 g. of product was decanted and distilled to give 250 g. MIBK and 410 g. TMNO boiling at 68°–71° C. at 4–5 mm. Remaining was 100 g. of higher boiling residue. The conversion was 70% with a yield of 80.4%.

This example illustrates that the aluminum oxycarbonate may also be utilized as a fluid bed rather than as a fixed bed catalyst.

EXAMPLE 13

The following equipment was used to form an aldol condensation unit:

A three liter flask was placed in a heating mantle. Extending from the flask was a 50 mm. diameter column. The column was packed at the bottom 1⅞" with Berl saddles, then for 10" with ⅛" by 8-mesh aluminum oxycarbonate and at the top 4⅞" with Berl saddles. A water-cooled condenser was attached to the top of the column.

To the flask was charged 1,800 ml. of methyl ethyl ketone (MEK) and refluxed at atmospheric pressure. A small amount of n-hexane added to the condenser aided separation of the water. After refluxing for 13 hours, approximately 70% of the original change was condensed to a product having a distinctive spicy odor. The condensation products were 5-methyl-4-hepten-3-one and 3, 4 dimethyl-3-hexen-2-one.

EXAMPLE 14

Utilizing the same equipment as in Example 13, the flask was charged with 1,600 ml. of n-butanal and 200 ml. of n-hexane. Refluxing at atmospheric pressure, the n-butanal was condensed to 2-ethylhexenal at approximately 20 g./hr.

EXAMPLE 15

Utilizing the same equipment as in Example 13, the flask was charged with 2,500 ml. mesityl oxide. Refluxing at atmospheric pressure resulted in a mixture of $C_9$ di-unsaturated ketones. The conversion rate was approximately 300 g./hr. In this example a substitution reaction took place and the distillate removed from the reaction was acetone rather than water.

EXAMPLE 16

The catalyst used in Example 1 was allowed to stand overnight and the reaction restarted. The rate of formation of TMNO was slightly more than 8 LB/hr/ft². After standing again overnight, the rate of TMNO formation was less than 8 LB/hr/ft². Loss of catalyst activity continued with subsequent stops and starts. In subsequent runs with $CO_2$ treatment of the catalyst at shutdown, no loss of activity occurred.

EXAMPLE 17

TMNO was heated in the presence of aluminum oxycarbonate using the same equipment as in Example 12. The material was decanted and distilled. The distillate consisted of MIBK, unreacted TMNO, $C_{18}$ diunsaturated ketones, and higher boiling materials.

EXAMPLE 18

Using the equipment from Example 15, 1500 ml cyclohexanone was charged to the flask with 100 g aluminum oxycarbonate. The flask was heated to an initial boiling point of 142 degrees C. Water evolved quickly and the temperature rose to 200 degrees C. in three hours. The fluid was decanted and distilled yielding unreacted cyclohexanone along with cyclohexylidene cyclohexanone and the higher condensation product $C_{18}H_{26}O$ believed to be dicyclohexylidene cyclohexanone.

EXAMPLE 19

Using the equipment from Example 16, 1500 ml cyclohexanone was charged to the flask and brought to reflux. After seven hours the pot temperature was 210 degrees C. containing about 80% cyclohexylidene cyclohexanone along with cyclohexanone and very little higher boiling material.

EXAMPLE 20

Using the equipment from example 15, 1700 ml acetophenone was charged along with 300 g. 1/8" catalyst. Then, 100 ml hexane was added to suppress the boiling point and azeotrpe the water. The aldol condensation was rapid with a yield of 65% phenyl beta methyl styryl ketone.

Thus the invention is primarily characterized by being more efficient and economical than any known commercial process for the described products, e.g., conversion of acetone to mesityl oxide. With the large quantities of mesityl oxide produced in the industry, this is a very important advantage. Simplicity of the process and required equipment now make smaller mesityl oxide plants possible as well as allowing flexibility in the location of the plants.

The invention efficiently produces materials for which no previously known method was commercially suitable, e.g., conversion of MIBK to TMNO.

The invention makes possible substitution of a carbonyl compound onto the alpha carbon of an alpha beta unsaturated carbonyl compound.

The nature and objects of the present invention having been completely described and illustrated and the best mode thereof contemplated set forth, what I wish to claim as new and useful and secure by Letters Patent is:

1. A process wherein a carbonyl compound is substituted onto the alpha-carbon of an alpha-beta unsaturated carbonyl compound by contacting said compounds with an aluminum oxycarbonate catalyst.

2. An aldol condensation-dehydration process for producing unsaturated carbonyl compounds comprising:

condensing two carbonyl molecules in the presence of an aluminum oxycarbonate catalyst to form an unsaturated carbonyl compound and water, at least one of said molecules having the formula:

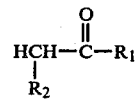

where $R_1$ and $R_2$ are selected from the group consisting of hydrogen, alkyl, alkylene, cycloalkyl, aryl, alkaryl and arakyl, and removing said water as it is being formed.

3. A process according to claim 2 wherein the reactivity of said catalyst is maintained and enhanced between usages by addition of $CO_2$ to the catalyst.

4. The process of claim 2 wherein said catalyst is in a fixed bed.

5. The process of claim 2 wherein said condensation is carried out in the presence of a solvent to aid the water removal.

6. The process of claim 1 wherein said carbonyl compound and said alpha-beta unsaturated carbonyl compound are mesityl oxide and said substitution process produces $C_9$-diunsaturated ketones.

7. The process according to claim 2 wherein said condensing and removing steps are carried out at a temperature range up to the decomposition point of said compound and at a predetermined pressure range.

8. The process according to claim 7 wherein said temperature range is between 0° C. and 200° C. and said pressure range is between less than one and fifty atmospheres.

9. The process according to claim 7 wherein said temperature range is between 80° C. and 150° C. and said pressure range is between 1 to 20 atmospheres.

10. A process according to claim 2 wherein said carbonyl molecules are methyl isobutyl ketone and said compound is trimethylnonen-one.

11. A process according to claim 2 wherein said carbonyl molecules are acetone and said compound is mesityl oxide.

12. A process according to claim 2 wherein said catalyst is in a fluid bed.

13. A process according to claim 2, wherein said carbonyl molecules are cyclohexanone and said compound is cyclohexylidene cyclohexanone.

14. A process according to claim 2, wherein said carbonyl molecules are acetophenone and said compound is phenyl beta methyl styryl ketone.

* * * * *